(12) United States Patent
Amberg et al.

(10) Patent No.: US 8,738,115 B2
(45) Date of Patent: May 27, 2014

(54) METHOD AND APPARATUS FOR SELECTIVE INTERNAL RADIATION THERAPY PLANNING AND IMPLEMENTATION

(75) Inventors: Jessica Amberg, Bubenreuth (DE); Yu Deuerling-Zheng, Erlangen (DE); Sigrid Ferschel, Uttenreuth (DE); Stefan Lautenschlaeger, Hausen (DE); Oliver Meissner, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 711 days.

(21) Appl. No.: 12/777,575

(22) Filed: May 11, 2010

(65) Prior Publication Data

US 2011/0282193 A1 Nov. 17, 2011

(51) Int. Cl.
*A61B 5/05* (2006.01)
(52) U.S. Cl.
USPC ............................. 600/427; 600/431; 604/508
(58) Field of Classification Search
USPC ......... 600/312, 317, 321, 325, 329, 407, 419, 600/420, 433, 436, 437, 454, 456; 424/1.11, 9.3
See application file for complete search history.

(56) References Cited

U.S. PATENT DOCUMENTS

| | | | | |
|---|---|---|---|---|
| 5,919,135 | A * | 7/1999 | Lemelson | 600/407 |
| 2003/0220569 | A1 * | 11/2003 | Dione et al. | 600/443 |
| 2004/0131543 | A1 * | 7/2004 | Wong et al. | 424/1.11 |
| 2004/0220135 | A1 * | 11/2004 | Gray | 514/50 |
| 2004/0258614 | A1 * | 12/2004 | Line et al. | 424/1.11 |
| 2007/0027390 | A1 * | 2/2007 | Maschke et al. | 600/425 |
| 2007/0167833 | A1 * | 7/2007 | Redel et al. | 600/476 |
| 2008/0021306 | A1 * | 1/2008 | Van Zijl et al. | 600/419 |
| 2008/0025952 | A1 * | 1/2008 | Scheule et al. | 424/93.2 |
| 2008/0031406 | A1 * | 2/2008 | Yan et al. | 378/14 |
| 2008/0200806 | A1 * | 8/2008 | Liu et al. | 600/439 |
| 2008/0247506 | A1 * | 10/2008 | Maschke | 378/15 |
| 2008/0262345 | A1 * | 10/2008 | Fichtinger et al. | 600/426 |
| 2009/0192385 | A1 * | 7/2009 | Meissner et al. | 600/426 |
| 2009/0287066 | A1 * | 11/2009 | Meissner et al. | 600/300 |

* cited by examiner

*Primary Examiner* — Unsu Jung
*Assistant Examiner* — Michael N Fisher
(74) *Attorney, Agent, or Firm* — Schiff Hardin LLP

(57) ABSTRACT

In a method and system for planning and implementing a selective internal radiation therapy (SIRT), the liver volume and the tumor volume are automatically calculated in a processor by analysis of items segmented from images obtained from the patient using one or more imaging modalities, with the administration of a contrast agent. The volume of therapeutic agent that is necessary to treat the tumor is automatically calculated from the liver volume, the tumor volume, and the body surface area of the patient and the lung shunt percentage for the patient. The therapeutic agent can be administered via respective feeder vessels in respectively different amounts that correspond to the percentage of blood supply to the tumor from the respective feeder vessels, this distribution also being automatically calculated by analysis of one or more parenchymal blood volume (PBV) images.

10 Claims, 4 Drawing Sheets

METHOD AND APPARATUS FOR SELECTIVE INTERNAL RADIATION THERAPY PLANNING AND IMPLEMENTATION

BACKGROUND OF THE INVENTION

1. Field of the Invention

The present invention concerns a method and an apparatus for planning and implementing selective internal radiation therapy (SIRT).

2. Description of the Prior Art

Interventional oncology provides an increasing number of minimally invasive treatment options, among them being a procedure called selective internal radiation therapy (SIRT).

SIRT is a non-surgical outpatient therapy that makes use of radioactive microspheres, called SIR-Spheres®, to deliver radiation directly to the site of one or more liver tumors. This targeted therapy preserves healthy tissue while delivering up to forty more times radiation to the liver tumors than would be possible using conventional radio-therapy.

It is very important for treating liver cancer to bring as much of the therapeutic agent (e.g. SIR-Spheres® in the case of SIRT) as possible to the tumor itself. It is also important, however, to prevent the surrounding tissues from being damaged by the destructive impact of the therapeutic agent. It is therefore very beneficial for the treating physician to have knowledge, which is as precise as possible, regarding the location of the tumor, and the location and anatomy of the tumor-feeding vessels (called "feeders"). In other words, it is extremely important to know the blood volume feeding the tumor.

In order to calculate the overall dose of the therapeutic agent (and to make a requisition for this amount of the therapeutic agent) the physician must also know information about the patient's height and weight, in order to calculate the body surface area (BSA), the volume of the entire volume (i.e. the complete organ), and the volume of each tumor to be treated. The determination of all of the above parameters is critical, because the more precise the dose delivery via the different feeders can be made, the better the outcome (i.e., therapy success).

Among the aforementioned factors, it would also be useful to know which of multiple feeding vessels supply which tumors, among multiple tumors, and how much liver volume is effected (fed) by each feeding vessel. The more exact the dose delivery can be made via the different tumor vessels, by advance calculation, the better effect the delivery of the therapeutic agent will have in treating the tumor or tumors. If the overall dose of the radioactive microspheres is split among the different feeding vessels according to their respective percentages with regard to feeding the tumor or tumors, the more effective the treatment can be made.

The conventional workflow for SIRT is as follows.

A pre-procedural computed-tomography (CT) imaging is implemented to visualize the tumor and its feeding vessels. A volume measurement is made using the pre-procedural CT dataset at a workstation, in order to identify the volume of the tumor and to then roughly estimate the amount of radioactive material that is required for the desired treatment. Although a quantitative blood volume measurement is available through the CT dataset, only the overall amount of radioactive material can be calculated because the blood volume measurement is performed with an intravenous injection. This means that the physician does not know how much of the overall dose needs to be introduced into the individual, respective feeding vessels.

A catheter intervention is then implemented in the angio-suite, in order to embolize the feeding vessels of the tumor with the radioactive microspheres. The patient is then transferred to the CT suite in order to control the embolization. A second catheter invention is made in the angio-suite, if the embolization result was not adequate. A final check of the overall procedural result is then made in the CT suite.

SUMMARY OF THE INVENTION

It is an object of the present invention to provide an improved method and apparatus for planning and implementing (SIRT).

The above object is achieved in accordance with the present invention by a procedure for planning and implementing SIRT, that includes the following steps. The patient is registered in the clinic or hospital in which the procedure is to be implemented, by obtaining demographic information including the patient's weight and height, so that the patient's body surface area (BSA) can be calculated.

A large volume scan of the patient is implemented that encompasses the acquisition of image data from the entire liver. This scan can be performed in the angio-suite using a robotic computed tomography system, such as a DynaCT®, which is commercially available from Siemens Healthcare. The scan of the entire liver can be implemented by executing the commercially available LargeVolume DynaCT®.

A commercially available image segmentation software tool is then used to automatically segment the liver, with no user interaction being necessary, so as to calculate the volume of the entire liver, using the image data acquired from the whole liver scan. The liver volume is thus known.

It is also possible to implement the aforementioned imaging and calculation steps using a previously acquired CT or magnetic resonance imaging (MRI) data set, or by using the so-called test-angio, which is conventionally performed approximately one week prior to the intervention (SIRT) in order to identify the feeding vessels to the tumor.

Contrast agent is then injected into the main branch of the tumor feeding vessel or vessels, with monitoring using the aforementioned LargeVolume robotic CT scan. The catheter is positioned in the main branch of the tumor feeding vessels so that the contrast agent is injected and the robotic LargeVolume scan is then implemented. The resulting volume dataset contains the contrast-enhanced tumor, as well as the contrast-enhanced feeders.

Using the contrast-enhanced dataset generated in the preceding step, a dedicated software tool calculates the volume of the tumor or tumors. If there are multiple tumors, each tumor is segmented by image segmenting with a different color, or with some other manner of separating them from each other. The result of this step is that the tumor volumes and location are known.

A dedicated software tool then calculates the center line/midline of each vessel feeding each tumor. This can be done either by selecting the tumor and the main branch of the tumor and the main branch of the tumor feeding vessel or vessels thereto, or by selecting only the main branch and using the segmentation result from the previous step. The result of this computation of the center line of the tumor feeding vessels is stored together with the corresponding segmentation of the tumor, obtained from the preceding step. This means that each tumor feeding vessel to each tumor is known.

During the aforementioned test-angio, it is conventional for the patient to be injected with radioactive material that has similar properties to the SIRT therapeutic agent (e.g. similar size), but which has a short radioactive half-life, and is administered in a much smaller dose than for the actual therapy. The distribution of this material in the test-angio is measured, typically in the nuclear medicine department of the clinic or hospital, in order to identify the percentage of the material that accumulates in the liver. This percentage is called the "lung shunt percentage." This value (typically between 0 and 40%) is needed to subsequently calculate the amount of therapeutic agent to be administered, in accordance with the inventive method.

In an optimized version of the inventive method, the lung can be segmented out of the dataset acquired with the large volume robotic CT scan, and registered or fused to the nuclear medical (PET or SPECT) volume. Having this registration/fusion provides an easy, fast and reliable way to measure the enrichment of the material in the lung. This step could be done in a combined system that includes a PET/SPECT modality with a conventional angio-system.

Based on the above information, there are several ways to calculate the necessary total amount of therapeutic agent to be administered, e.g. SIRSpheres®. The formula used to calculate the amount of therapeutic agent to be administered can be adjusted individually by the physician.

At this point, if the procedure is being implemented automatically, a check can be made as to whether the BSA of the patient is known. If the patient's weight and height were not entered in the registration step, a user can enter these values at this time.

The calculated amount of the therapeutic agent is then requisitioned by the physician, in order to implement the subsequent steps.

The segmented tumor or tumors and feeding vessel or vessels are overlaid on a live fluoroscopic image that is acquired during the interventional procedure. This can be done, for example, by operating a fluoroscopic imaging system according to Syngo® Pilot, commercially available from Siemens Healthcare. If the tumor segmentation and feeder detection were performed with volumes that were acquired during the test-angio, the physician must acquire a LargeVolume® scan in this step as well, in order to register/fuse the tumors and feeders with the currently acquired LargeVolume® scan.

The requisitioned amount of the therapeutic agent, such as SIR-Spheres® is then administered to the patient.

As noted above, the calculation of the amount of therapeutic agent that must be requisitioned and administered can proceed in a number of ways. In a preferred embodiment of the invention, this calculation is undertaken as follows, in a manner that is not conventional and that encompassed as part of the inventive method.

In this inventive embodiment, a parenchymal blood volume (PBV) scan of the liver is implemented. This general type of scan is a standard CT application for brain imaging, known as "neuroPBV." By applying this type of scan to the liver, an image is generated that allows the blood volume distribution in the liver to be quantitatively determined, dependent on the amount of contrast agent that is injected into the corresponding feeders. In a PBV scan, the resulting image shows the blood volume distribution in different colors, with each color representing a level of blood volume.

The necessary PBV scan can be implemented with the aforementioned robotic CT system (DynaCT LargeVolume scan), with contrast agent successively injected into each of the feeders for the tumor. Each scan for each contrast agent injection for each feeder will show the resulting amount of blood distribution in the liver that results from that feeder.

As an example, it can be assumed that a liver tumor in question has four feeders. Without knowing precisely how each of these four vessels delivers (supplies) blood to the tumor, the physician would administer 25% of the overall total of therapeutic agent (microspheres) to each of the four feeders. From the information obtained by the aforementioned PBV scans in accordance with the invention, however, the physician can determine, for example, that one of the feeders supplies the tumor with 40% of its blood, and the other three feeders each supply the tumor with 20% of its blood. The physician can then distribute the administration of the therapeutic agent according to this supply percentage, by administering 40% of the therapeutic agent via the first-noted feeder, and administering 20% of the total of the therapeutic agent to each of the other three feeders.

This embodiment not only optimizes the success of the SIRT, but also avoids excessive use (and thus increased cost) of the therapeutic agent by correlating the administration of the therapeutic agent with the actual blood supply to the tumor.

The invention also encompasses an imaging/interventional apparatus that is designed to perform all of the aforementioned method steps and embodiments. Such a system can be, for example, a LargeVolume robotic CT system (Dynascan®), with a power injector operated by the same control unit (control console) that operates the imaging modality. The control unit is computerized, and is programmed to implement the aforementioned inventive method steps and all embodiments thereof.

DESCRIPTION OF THE PREFERRED EMBODIMENTS

Figure 1:
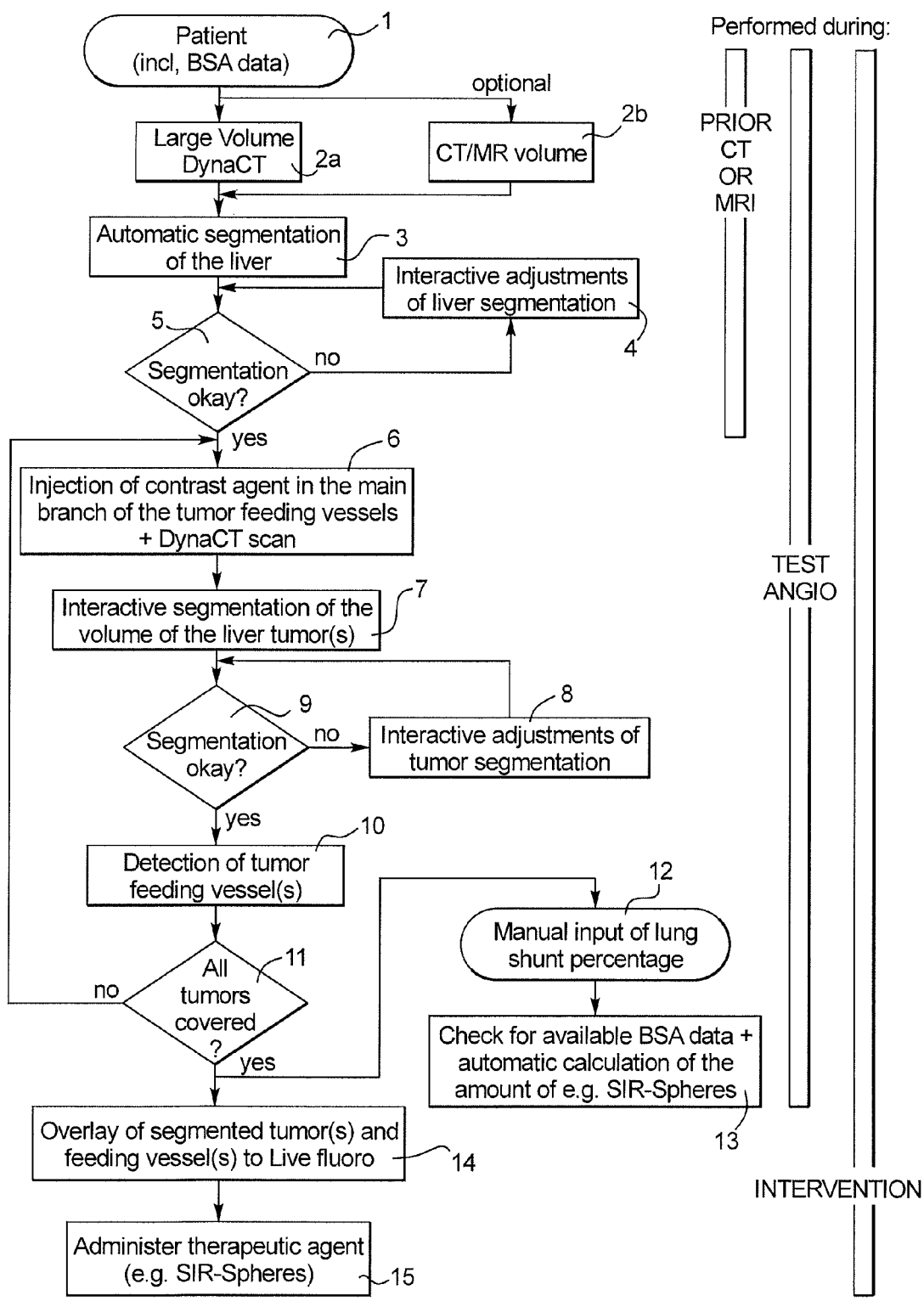
FIG. 1 is a flowchart schematically illustrating the basic steps in an embodiment of the invention for planning and implementing SIRT.

As shown in FIG. 1, the method according to the invention preferably begins in step 1 with patient registration, wherein at least enough demographic information is acquired from the patient so as to be able to calculate the patient's body surface area (BSA). This means that at least the patient's weight W and height H must be known. Typically, the body surface area is calculated as BSA $(m^2) = (W \cdot H/3600)^{1/2}$. As described below, although it is preferable to acquire this information initially during the course of the patient registration in step 1, it is also possible to manually enter this information at a later point in time within the overall method.

In step 2a, a large volume scan of the patient is implemented, such as using a robotic CT system of the type commercially available from Siemens Healthcare under the designation DynaCT®. This scan encompasses the entire liver of the patient.

Optionally, as indicated in step 2b, the volume dataset encompassing the liver can be obtained from a previously-generated CT or MR volume scan.

In step 3, a software tool is implemented for image segmentation of the liver, with no user interaction. The image segmentation calculates the volume of the entire liver using the volume information acquired in step 2a or 2b. As indicated in step 4, although it is preferable for no user interaction to be needed in this step, it is possible to make interactive adjustments of the liver segmentation to improve the segmentation result, if necessary. For this purpose, a check can be made in step 5 as to whether the segmentation is acceptable. If not, interactive adjustments may be required in step 4. If the segmentation is acceptable either directly from the information provided in step 3, or with the interactive adjustments made in step 4, the method proceeds to step 6, wherein contrast agent is injected in the main branch of the tumor feeding vessel or vessels. This contrast agent injection is implemented with large volume CT monitoring, again preferably using a DynaCT® system. In step 6, the catheter is positioned in the main branch of the tumor feeding vessel or Vessels, so that the contrast agent is injected into that vessel. The resulting volume scan thus shows the contrast-enhanced tumor, as well as the contrast-enhanced feeders.

In step 7, an interactive segmentation of the volume of the liver tumor takes place with user interaction, using a software tool. If there are multiple tumors, each tumor is segmented with a different color, in order to separate them from each other. Again, a check is made in step 9 to determine if and when the segmentation is acceptable, with further interactive adjustments, if necessary, being implemented in step 8.

As a result of step 9, the tumor volume (or tumor volumes) and location thereof are known.

In step 10, a dedicated software tool calculates the center line/midline of the vessel or vessels feeding each tumor. This can be done either by selecting the tumor and the main branch of its tumor feeding vessels, or by selecting only the main branch and taking the segmentation result from step 9 into account. The result of this computation of the center line of the tumor feeding vessels is stored, together with the corresponding segmentation of the tumor. This means that the parameter representing the tumor feeding vessels is known. As indicated in step 11, this is repeated, as necessary, until the information for all tumors is obtained.

In step 12, a manual injection takes place in order to determine the lung shunt percentage. For this purpose, radioactive material is injected into the patient that has similar properties as the therapeutic agent that would be administered for SIRT, but with a very short radioactive half-life, and at a much lower dose. The distribution of this material is measured, such as in the nuclear medicine department of the hospital or clinic, in order to determine the percentage of this material that accumulates in the liver. This percentage is called the "lung shunt percentage," and typically has a value between 0 and 40%.

Following step 12, a check can be made as to whether the data for calculating the BSA of the patient is known. If hot, the height and weight of the patient can be manually entered in step 13.

In step 14, the segmented tumor or tumors and feeding vessel or vessels are overlaid on a live fluoroscopic image of the patient, acquired during the therapy intervention procedure. If the tumor segmentation and feeder identification have been performed with volumes, which have been acquired during the test-angio, the physician needs to acquire a LargeVolume CT image as well. This LargeVolume CT is needed to register/fuse the tumors and feeders with the currently acquired image. This step is needed in order to achieve an exact overlay of the tumors and the feeders with the live fluoro images.

In step 15, the therapeutic agent, such as SIRSpheres® is administered in an amount that has been exactly calculated based on the patient's BSA, the volume of the entire liver, and the volume of each tumor to be treated.

As indicated at the right side of FIG. 1, the initial steps can be performed with information obtained from a prior CT or MRI scan, and a large number of the steps can be performed in the test-angio that is always implemented approximately one week before an SIRT procedure. Preferably, however, all of the steps are performed in one intervention procedure, with all modalities necessary to implement the method being present in the angio-suite, with the exception of the nuclear medicine equipment needed to determine the lung shunt percentage. There is no need to transfer the patient back and forth among different imaging modalities.

All of the aforementioned dedicated software tools are available with the DynaCT® system. Because of the accurate calculation and requisition of the therapeutic agent, unnecessary use of excessive therapeutic agent is avoided, thereby saving cost. The procedure can be implemented more quickly than conventional procedures, thereby placing less stress on the patient, and allowing the physician, or those in the physician's facility, to more accurately plan ahead to reserve the necessary equipment and room occupation.

Figure 2:
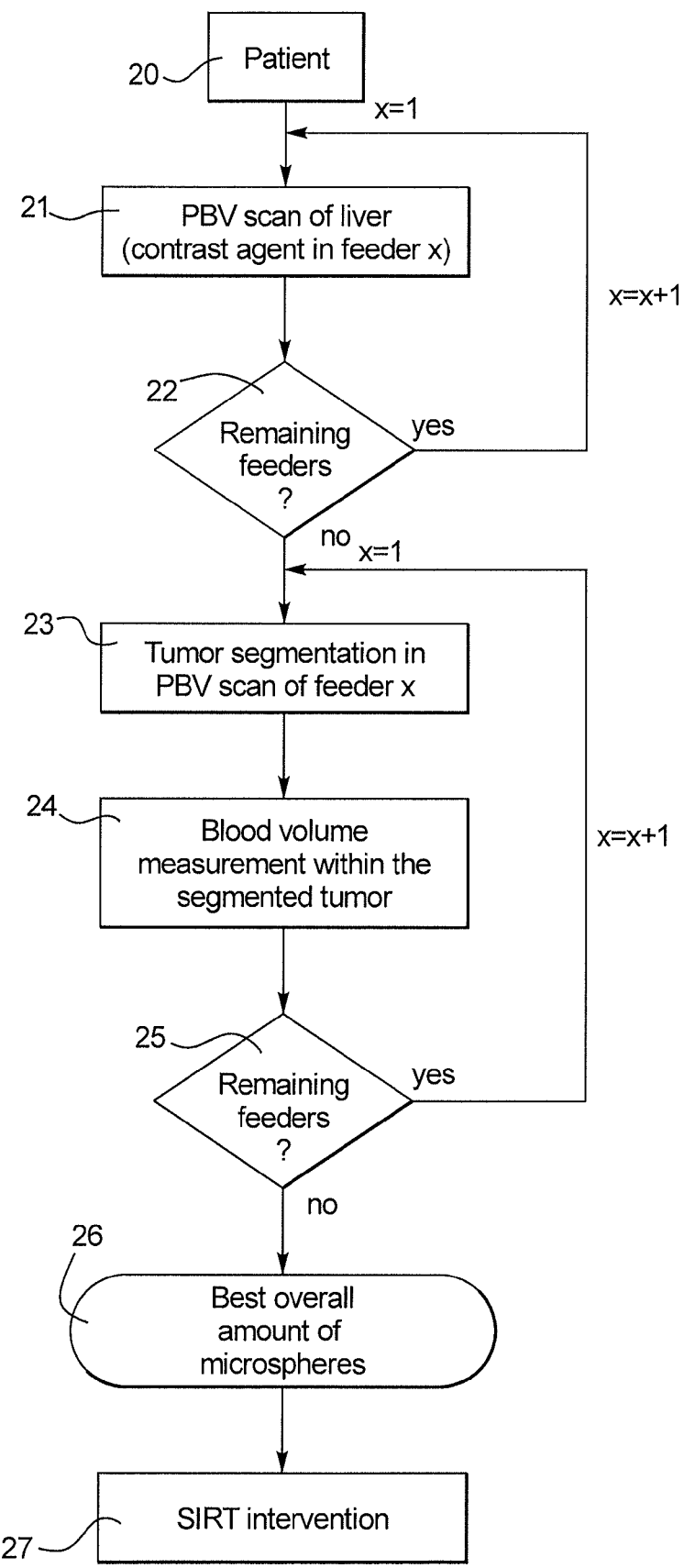
FIG. 2 is a flowchart schematically illustrating an embodiment of the invention for matching administration of the SIRT therapeutic agent to the distribution of blood supply to the tumor via respective feeder vessels.
Figure 3:
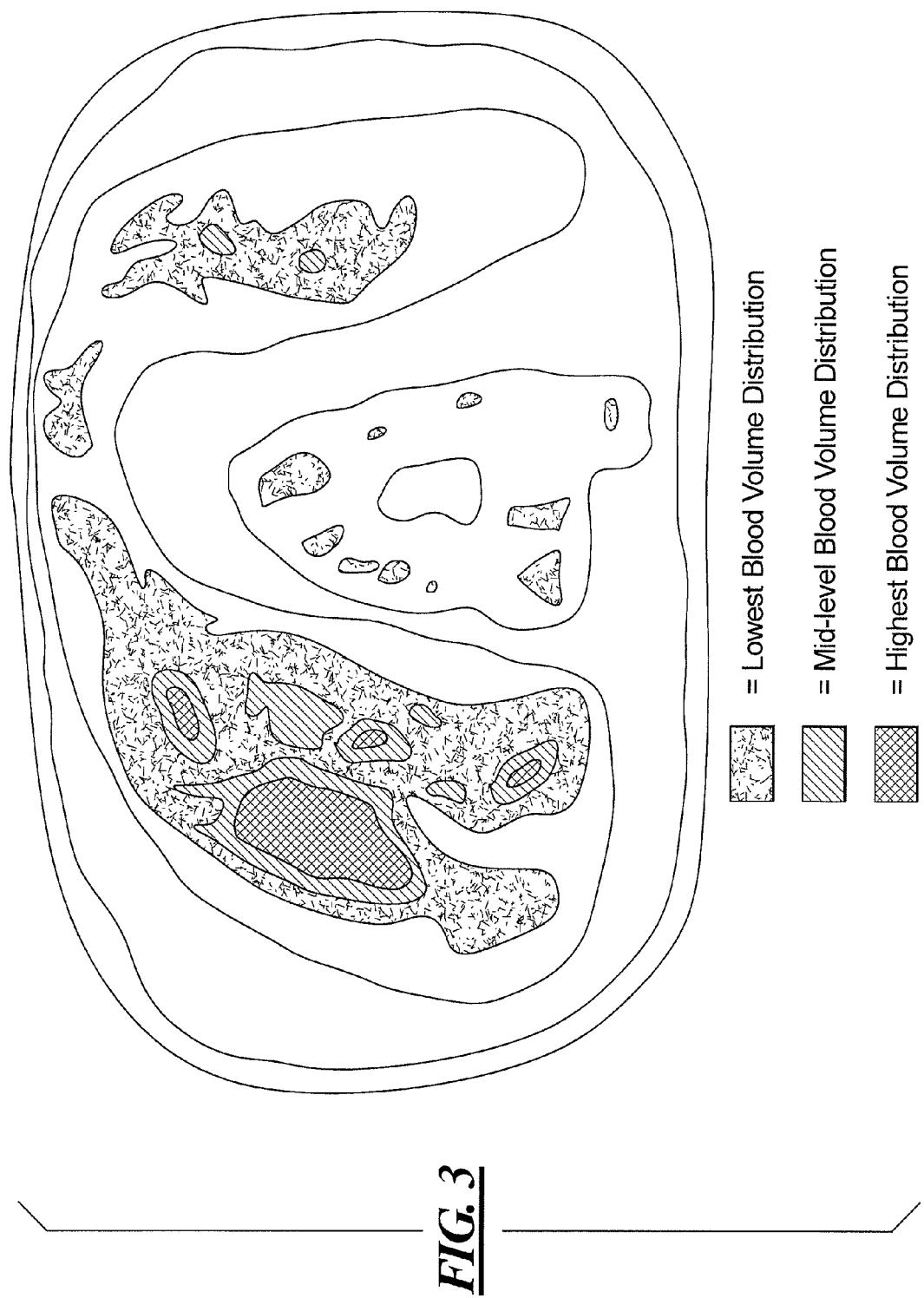
FIG. 3 is an example of a PBV image of the liver acquired in the embodiment of the method shown in FIG. 2.

FIG. 2 shows the basic steps in an embodiment of the inventive method for identifying the optimum distribution of administration of therapeutic agent in SIRT among respective feeders to a tumor in the liver. This embodiment of the invention makes use of a PVB scan of the liver, as schematically illustrated in FIG. 3, and as explained in more detail below. The PBV scan of the liver takes place for a patient 20 in step 21, a PBC scan of the liver is acquired for each feeder x to the liver. Each PBV scan produces a result as shown in the example of FIG. 3 providing a visual representation of the blood volume distribution in the liver that results from the feeder into which the contrast agent has been injected. In actuality, the different levels of blood volume will be identified by different colors, with the "warmer" the colors get, the more blood volume is located in the corresponding area. Instead of colors, FIG. 3 indicates different blood volume distribution levels by stippling, hatching, and cross-hatching.

In step 22, step 21 is repeated for each feeder to the liver, until there are no remaining feeders.

In step 23, image segmentation of the tumor is undertaken so that the tumor is segmented (separated from) the image of the overall liver. By overlying the segmented tumor on the PBV scan of the type shown in FIG. 3, it can be seen whether the feeder, to which the contrast agent was administered in order to produce the PBV scan, is a significant source of blood supply to the tumor. This can be directly quantitatively identified by calculating the blood volume within the overlaid tumor, depending on the feeder.

As indicated in step 25, this procedure is repeated for each PBV scan representing each of the feeders, until calculations for each feeder for the particular tumor in question have been taken into account. If multiple tumors are present, the same procedure can be repeated for each separately segmented tumor.

From the calculated volume of blood supply to the tumor from each of the feeders, a determination is then made in step 26 as to the optimum amount of microspheres (therapeutic agent) that should be administered to each of the respective feeders. The physician knows how much of the total blood supply to the tumor results from each feeder, and the administration of the microspheres in the respective feeders is then distributed according to the same distribution represented by the blood supply percentages.

The SIRT intervention is then implemented in step 27 with the microspheres administered according to the distribution determined in step 26.

Figure 4:
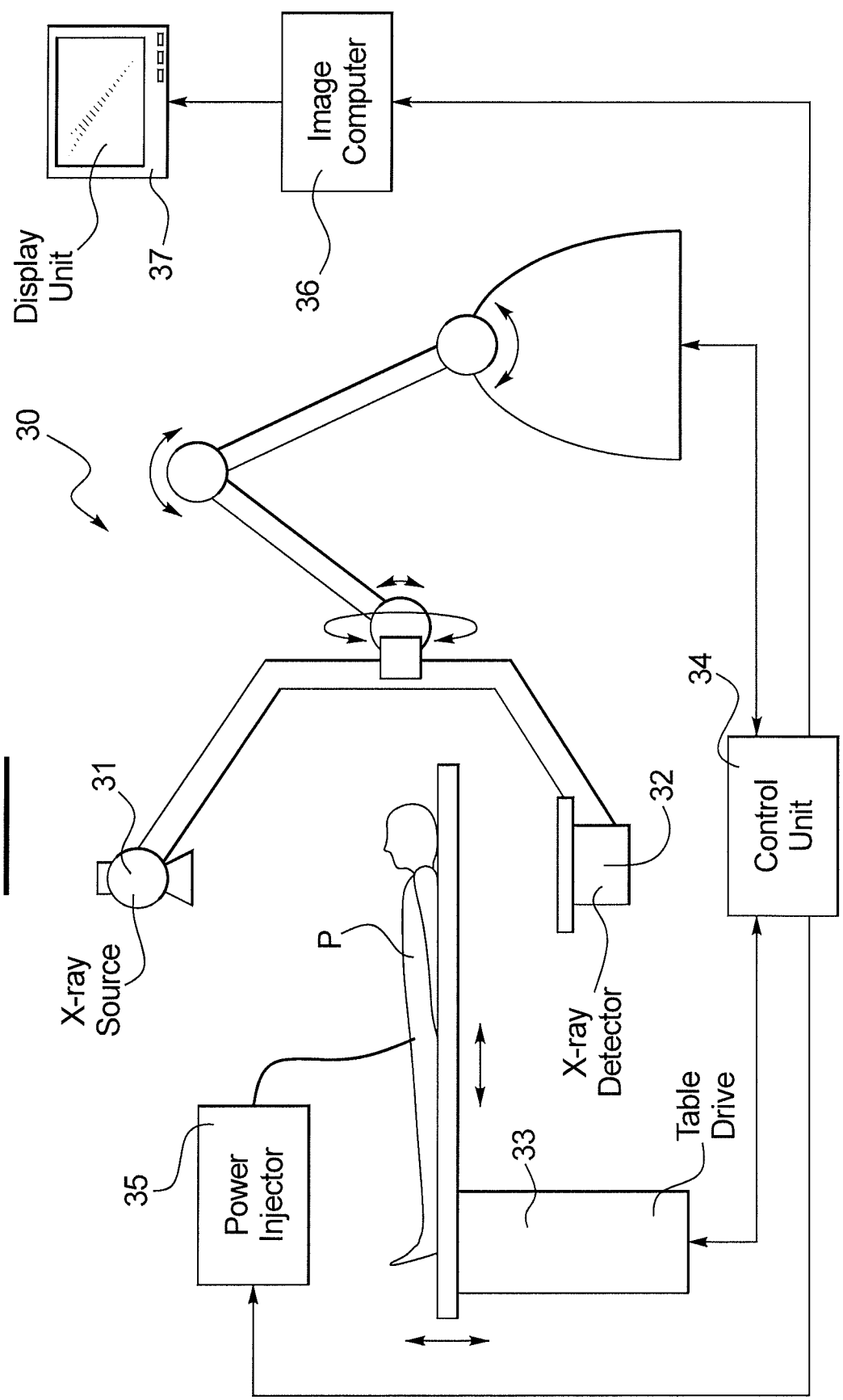
FIG. 4 schematically illustrates a LargeVolume CT imaging modality, with a power injector, constructed and operating in accordance with the present invention.

FIG. 4 schematically illustrates the basic components of a system for implementing the methods described above. The system can be generically described as a robotic CT system 30, of which the aforementioned DynaCT® system that is commercially available from Siemens Healthcare is an example. The robotic CT system 30 has a C-arm on which an x-ray source 31 and a radiation detector 32 are mounted. The C-arm is movable in many different directions and configurations by an articulated robot arm assembly, that has three articulated joints allowing movement as indicated by the double arrows, as well as rotational movement of the C-arm.

A patient P is supported on a patient table that is movable by a table drive 33. The robotic CT system 30 and the table drive 33 are operated by a control unit 34, which also receives the image data from the x-ray detector 32. The control unit 34 also controls operation of a power injector 35, that can be used to administer the contrast agent for the purposes described above, as well as to administer the therapeutic agent, as described above.

The control unit 34 is in communication with an image computer 36 that generates the images as described above and displays those images on a display unit 37. The image computer 36 can be, for example, a computer workstation having an appropriate user interface allowing the data and information entries described above to be made. Moreover, the image computer 36 and the control unit 34 may be integrated as a single computer system. The control unit 34 and/or the image computer 36 are appropriately programmed to implement the method described above, including all embodiments thereof.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for planning and implementing a selective internal radiation therapy (SIRT), comprising the steps of:
   providing a processor with a large volume dataset of a patient who is to undergo SIRT, said large volume dataset encompassing the entire liver of the patient, said liver having a tumor therein fed with blood by feeder vessels emanating from a main branch;
   in the processor, automatically segmenting the liver from surrounding tissue in said large volume dataset by executing a computerize segmentation algorithm, and automatically calculating the volume of the liver from the segmented liver;
   injecting contrast agent into said main branch for said feeder vessels and acquiring a contrast-enhanced tomographic volume dataset from the patient comprising a contrast-enhanced tumor and contrast-enhanced feeder vessels that supply blood to said contrast-enhanced tumor;
   in said processor, automatically segmenting said contrast-enhanced tumor and said contrast-enhanced feeder vessels from surrounding tissue in said contrast-enhanced volume dataset by executing a computerize segmentation algorithm;
   in said processor, automatically calculating the volume of the tumor from the segmented contrast-enhanced tumor;
   determining a lung shunt percentage for said patient;
   determining the body surface area (BSA) of the patient;
   in said processor, automatically calculating an amount of therapeutic agent for use in said SIRT for treating said tumor, from the BSA, the lung shunt percentage, the liver volume, and the tumor volume;
   obtaining a live fluoroscopic image of the liver of the patient during SIRT and overlaying the segmented contrast-enhanced liver and the segmented contrast-enhanced feeder vessels on said live fluoroscopic image, to obtain an overlay image;
   using said overlay image, positioning a catheter with respect to at least one of said feeder vessels; and
   via said catheter, administering the calculated amount of said therapeutic agent during SIRT.

2. A method as claimed in claim 1 comprising calculating a volume of radioactive microspheres as said therapeutic agent, and administering the calculated volume of radioactive microspheres during SIRT.

3. A method as claimed in claim 1 comprising acquiring each of said large volume dataset and said contrast-enhanced volume dataset using a robotic computed tomography system.

4. A method as claimed in claim 1 comprising, during SIRT, acquiring a further tomographic volume dataset encompassing the liver of the patient and using said further tomographic volume dataset to overlay said segmented contrast-enhanced tumor and said segmented contrast-enhanced feeder vessels on said live fluoroscopic image with an anatomically correct, for said patient, registration with respect to the liver in said overlay image.

5. A method as claimed in claim 1 comprising:
   for each tumor and for each feeder vessel feeding each tumor, acquiring a parenchymal blood volume (PBV) scan of the liver of the patient using an imaging modality with contrast-agent injected successively into each of said feeder vessels;
   in said processor, automatically analyzing each of said PBV scans to identify a percentage of blood supply to each tumor produced by each of said feeder vessels; and
   controlling administration of said therapeutic agent to administer respective amounts of said therapeutic agent to said tumor via the respective feeder vessels thereto corresponding to the percentage of blood supplied to the tumor by each of said feeder vessels.

6. A system for planning and implementing a selective internal radiation therapy (SIRT), comprising:
   a tomographic imaging modality;
   a control unit configured to operate said tomographic imaging modality to generate a large volume dataset of a patient who is to undergo SIRT, said large volume dataset encompassing the entire liver of the patient, said liver having a tumor therein fed with blood by feeder vessels emanating from a main branch;
   a processor supplied with said large volume dataset and configured to automatically segment the liver from surrounding tissue in said large volume dataset by executing a computerize segmentation algorithm, and automatically calculate the volume of the liver from the segmented liver;
   a contrast agent injector;
   said control unit being configured to operate said tomographic imaging modality and said contrast agent injector to inject contrast agent into said main branch for said feeder vessels and to acquire a contrast-enhanced tomographic volume dataset from the patient comprising a contrast-enhanced tumor and contrast-enhanced feeder vessels that supply blood to said contrast-enhanced tumor;
   said processor being configured to automatically segment said contrast-enhanced tumor and said contrast-enhanced feeder vessels from surrounding tissue in said contrast-enhanced volume dataset by executing a computerize segmentation algorithm;

said processor being configured to automatically calculate the volume of the tumor from the segmented contrast-enhanced tumor;

said processor also being supplied with an input representing a lung shunt percentage for said patient and an input representing the body surface area (BSA) of the patient, and said processor being configured to automatically calculate an amount of therapeutic agent for use in said SIRT for treating said tumor, from the BSA, the lung shunt percentage, the liver volume, and the tumor volume;

a fluoroscopic imaging modality configured to obtain a live fluoroscopic image of the liver of the patient during SIRT and to overlay the segmented contrast-enhanced liver and the segmented contrast-enhanced feeder vessels on said live fluoroscopic image, to obtain an overlay image;

a catheter that is positioned dependent on said overlay image, with respect to at least one of said feeder vessels; and said catheter being connected to a source of said therapeutic agent and being operated to administer the calculated amount of said therapeutic agent during SIRT.

7. A system as claimed in claim 6 wherein said processor is configured to calculate a volume of radioactive microspheres as said therapeutic agent, and wherein said source of therapeutic agent is a source of said radioactive microspheres.

8. A system as claimed in claim 6 wherein said tomographic imaging modality is a robotic computed tomography system.

9. A system as claimed in claim 6 wherein said control unit is configured to operate said tomographic imaging modality during SIRT to acquire a further tomographic volume dataset encompassing the liver of the patient and wherein said fluoroscopic imaging modality is configured to use said further tomographic volume dataset to overlay said segmented contrast-enhanced tumor and said segmented contrast-enhanced feeder vessels on said live fluoroscopic image with an anatomically correct, for said patient, registration with respect to the liver in said overlay image.

10. A system as claimed in claim 6 wherein:

said control unit is configured to operate said tomographic imaging modality and said contrast agent injector to acquire for each tumor and for each feeder vessel feeding each tumor, a parenchymal blood volume (PBV) scan of the liver of the patient with contrast-agent injected successively into each of said feeder vessels;

said processor is configured to automatically analyze each of said PBV scans to identify a percentage of blood supply to each tumor produced by each of said feeder vessels; and said catheter is successively positionable with respect to each of said feeder vessels to administer respective amounts of said therapeutic agent to said tumor via the respective feeder vessels thereto corresponding to the percentage of blood supplied to the tumor by each of said feeder vessels.

* * * * *